United States Patent [19]

Rachman

[11] Patent Number: 5,972,325

[45] Date of Patent: Oct. 26, 1999

[54] METHOD FOR SKIN TREATMENT

[76] Inventor: Paul Rachman, P.O. Box 34012, Houston, Tex. 77234

[21] Appl. No.: 09/326,715

[22] Filed: Jun. 7, 1999

[51] Int. Cl.⁶ .............................. A61K 31/74; A61F 7/00
[52] U.S. Cl. ........................................ 424/78.03; 607/109
[58] Field of Search .......................... 607/109; 424/78.03

[56] References Cited

U.S. PATENT DOCUMENTS

| | | |
|---|---|---|
| 686,670 | 11/1901 | Fitzgerald . |
| 1,758,286 | 5/1930 | Larson . |
| 2,252,423 | 8/1941 | Baddour ................................... 219/46 |
| 4,614,189 | 9/1986 | MacKenzie ............................. 128/380 |
| 5,879,379 | 3/1999 | Mason et al. ........................... 607/109 |

*Primary Examiner*—Raymond Henley, III
*Attorney, Agent, or Firm*—Russell J. Egan

[57] ABSTRACT

A method for skin treatment consists of the steps of applying a moisturizing cream to the face, covering the face from the scalp to the neck with a soft light weight moist towel, covering this towel with a plastic sheet, and applying towels soaked in very hot water to the plastic sheet slowly bringing the temperature up to a level comfortable to the client and maintaining this temperature by continuously replacing the hot towels for a period sufficient to perform the skin treatment. The towels and plastic sheet are then removed and the face cleansed of the material drawn from the pores.

8 Claims, 2 Drawing Sheets

METHOD FOR SKIN TREATMENT

BACKGROUND OF THE INVENTION

1. The Field of the Invention

This invention relates to a method for treating skin to both cleanse and revitalize the skin and, in particular, to a method for treating skin through the use of hot moisture.

2. Background of the Invention

It has long been known that warm moisture is good for the skin and improves the complexion. However, heretofore the methods and apparatus for applying warm moisture to skin have ranged from being uncomfortable to being dangerous. For example, U.S. Pat. No. 686,670 to Fitzgerald shows a device in which live steam is applied directly to the face, head and scalp. Clearly misuse of such a device could cause serious injuries. U.S. Pat. Nos. 1,758,286 to Larson and 2,252,423 to Baddour both show electrically heated masks which are to be placed over the face to supply heat thereto. These devices do not provide the necessary moisture to the skin and could become dangerous if used in conjunction with moisture. U.S. Pat. Nos. 4,614,189 to MacKenzie and 5,879,379 to Mason et al both show facial packs which can be used to apply either heat of cold to facial areas. However, both devices lack the capacity to provide moisture to the treated areas of the skin.

BRIEF SUMMARY OF THE INVENTION

In accordance with the present invention, the method for skin treatment consists of the steps of applying a moisturizing cream to the face, providing breathing means to the nose, covering the face from the scalp to the neck with a soft, light weight, moist towel; covering this towel with an impervious plastic sheet, and applying a plurality of hot moist towels on top of the plastic sheet to slowly bring the temperature under the plastic sheet up to a level comfortable to the client and maintaining this temperature by continuously replacing the hot towels with fresh hot towels. The hot towels are soaked in very hot water, removed and the excess water squeezed from each towel before it is applied to the plastic sheet. This step of applying hot towels lasts for a period sufficient to perform the skin treatment, about 45 to 60 minutes but which will vary for each client. At the end of the desired time period, the towels in place are allowed to cool gradually lowering the temperature under the plastic sheet. The cooled towels, plastic sheet, and soft towel are then removed. The face will have the appearance of being covered with a plurality of sprouts of the material drawn from the pores by this cleansing process. The face and neck are then cleansed of the material drawn from the pores.

Therefor it is an object of the present invention to provide a skin treatment method which applies moist heat to the face in a safe and controlled manner.

The foregoing and other objects and advantages of the invention will appear in the following detailed description.

BRIEF DESCRIPTION OF THE DRAWINGS

The present invention will be described, by way of example, with reference to the accompanying drawings, in which.

DETAILED DESCRIPTION OF AN EMBODIMENT OF THE INVENTION

Figure 1:
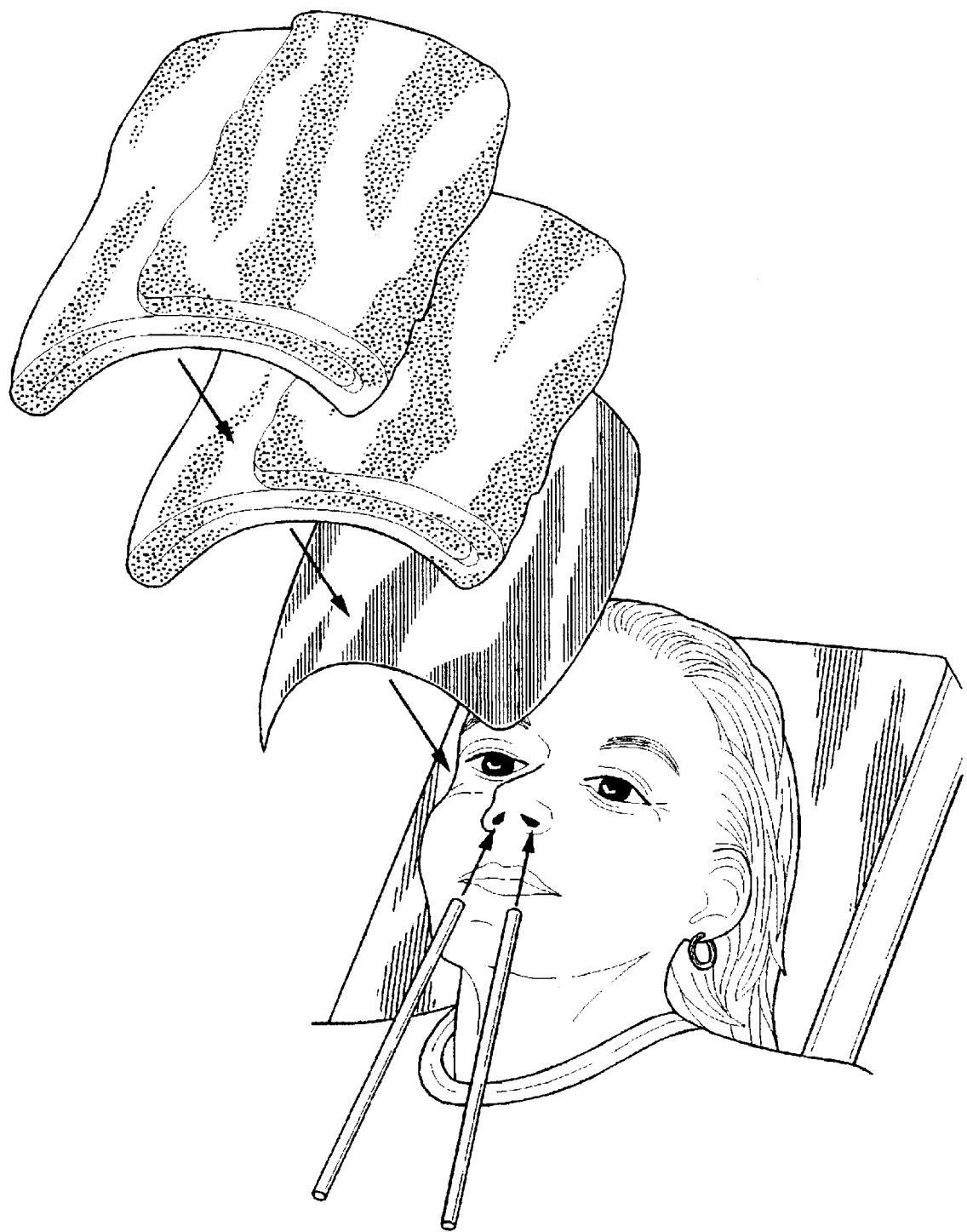
FIG. 1 is an exploded perspective view of the elements of the present invention.
Figure 2:
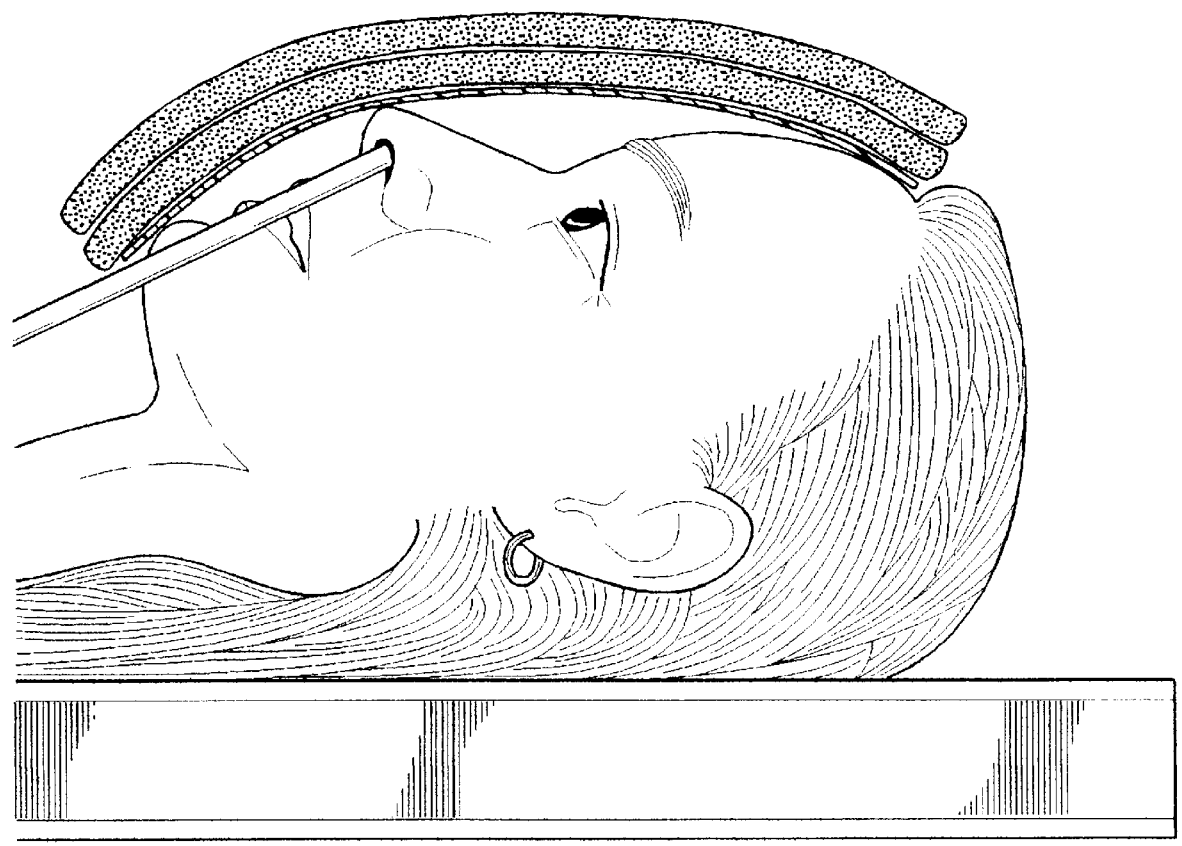
FIG. 2 is a side elevation, partially in section, showing the elements of the invention in place.

With reference to the Figures, the present invention is a method for skin treatment in which the client is positioned comfortably in a reclining chair such as those found in hair salons and/or dentist offices. A moisturizing cream (not shown) is applied all over the entire face and neck. Breathing means 10, such as the tubes or straws shown or any type of known oxygen mask (not shown), is applied into the nostrils. The face from the scalp to the neck is next covered with a soft, light weight, moist towel 12. This towel 12 is then covered with an impervious plastic sheet 14, which is of sufficient rigidity that it will not mold to the face. Then hot moist towels 16, 18 are applied on top of the plastic sheet 14 slowly bringing the temperature below the plastic sheet up to a level comfortable to the client. This temperature is maintained by continuously replacing the hot towels 16, 18 with fresh hot towels for a period sufficient to perform the skin treatment. At the end of the desired treatment time, the towels 16, 18 in place are allowed to cool down, approximately five minutes, before they, the plastic sheet 14 and the soft towel 12 are removed. The treated area will have the appearance of a plurality of stalks of material projecting form the pores and the face cleansed of the material drawn from the pores.

The towels 16, 18 are preferably heated by soaking in a tub of hot, even boiling, water with each towel, as needed, being removed from the hot water, squeezed to remove excess hot water, and placed on the plastic sheet.

The client lies on a reclining chair, such as hair stylist or dentist use, preferably at an angle of about 45°. A thin layer of moisturizing cream is applied to the client's face and neck area. Preferably this is a water-based cream. A thin, light weight, moist towel 12 is placed over the face and neck and an impervious sheet of plastic 14, of moderate thickness, is placed over the towel 12. Then a series of small to medium sized towels 16, 18, from a supply in a nearby pot of hot, i.e., boiling, boiling water, is withdrawn from the supply one at a time, the excess water squeezed out, and placed on the plastic sheet slowly bring up the temperature of the client's skin. The hot damp towels are replaced as they cool so that the client's face and neck stay close to the desired temperature throughout the entire treatment. The moisturizing cream and the damp light weight towel 12 under the plastic sheet 14 generate hot vapor that is trapped under the plastic sheet by the weight of the towels 16, 18 on top of the plastic sheet 14.

As the towels cool, they are replaced by fresh hot towels in order to maintain the level of heat that the client can take. This process lasts in the range of 45 to 60 minutes followed by a five minute cooling down period during which the last towels placed are allowed to cool down and are not replaced. Then the cooled towels 16, 18, plastic sheet 14 and light weight towel 12 are removed. The face and neck of the client will have the appearance of a plurality of individual stalks of material drawn from the pores. The face and neck are then washed thoroughly with a moist face cloth with the client now feeling quite relaxed and rejuvenated.

The present invention may be subject to many modifications and changes without departing from the spirit or essential characteristics thereof The present embodiment should therefore be considered in all respects as illustrative and not restrictive of the scope of the invention as defined by the appended claims.

I claim:

1. A method for treating skin comprising the steps of:

covering the face and neck area with a moisturizing cream;

placing breathing means to the nostrils;

covering the face and neck with a damp light weight cloth;

covering the cloth with a flexible plastic sheet forming a tent above the face and neck; and applying hot wet towels to the plastic sheet to raise the temperature of the skin on the face and neck.

2. The method according to claim 1 wherein said moisturizing cream is water based.

3. The method according to claim 1 wherein the hot towels remain in place 45 to 60 minutes.

4. The method according to claim 1 wherein the hot towels, as they cool, are systematically replaced to maintain the temperature of the face and neck at an elevated state.

5. The method according to claim 1 wherein the hot towels are heated by placing into a container of boiling water, with the excess water being squeezed from each towel prior to being placed on the plastic sheet.

6. The method according to claim 1 wherein the treatment ends with a cool down period during which the last towels remain in place until cool.

7. The method according to claim 6 wherein said cool down period is approximately five minutes in duration.

8. The method according to claim 6 further comprising the step of cleansing the face and neck thoroughly to remove all of the material drawn from the pores by this method.

* * * * *